United States Patent
Chen et al.

(10) Patent No.: US 11,969,727 B2
(45) Date of Patent: Apr. 30, 2024

(54) TUMOR MICROENVIRONMENT ON CHIP

(71) Applicants: China Medical University, Taichung (TW); China Medical University Hospital, Taichung (TW)

(72) Inventors: Yi-Wen Chen, Taichung (TW); Ming-You Shie, Taichung (TW); Der-Yang Cho, Taichung (TW); Shao-Chih Chiu, Taichung (TW); Kai-Wen Kan, Taichung (TW); Chien-Chang Chen, Taichung (TW)

(73) Assignees: China Medical University, Taichung (TW); China Medical University Hospital, Taichung (TW)

( * ) Notice: Subject to any disclaimer, the term of this patent is extended or adjusted under 35 U.S.C. 154(b) by 143 days.

(21) Appl. No.: 17/508,020

(22) Filed: Oct. 22, 2021

(65) Prior Publication Data

US 2023/0008649 A1 Jan. 12, 2023

(30) Foreign Application Priority Data

Jul. 9, 2021 (TW) ................................. 110125222

(51) Int. Cl.
| | | |
|---|---|---|
| *B01L 3/00* | (2006.01) | |
| *C12N 5/078* | (2010.01) | |
| *C12N 5/09* | (2010.01) | |
| *G01N 33/50* | (2006.01) | |

(52) U.S. Cl.
CPC ...... *B01L 3/502707* (2013.01); *C12N 5/0634* (2013.01); *C12N 5/0693* (2013.01); *B01L 2200/12* (2013.01); *B01L 2300/0636* (2013.01); *B01L 2300/069* (2013.01); *B01L 2300/0819* (2013.01); *G01N 33/5008* (2013.01)

(58) Field of Classification Search
None
See application file for complete search history.

(56) References Cited

U.S. PATENT DOCUMENTS

| | | | |
|---|---|---|---|
| 6,210,910 B1 * | 4/2001 | Walt | G01N 33/54373 |
| | | | 436/805 |
| 9,151,714 B2 | 10/2015 | Park et al. | |
| 10,022,717 B2 | 7/2018 | Park et al. | |
| 10,730,042 B2 | 8/2020 | Huang et al. | |
| 11,192,083 B2 | 12/2021 | Kraft et al. | |
| 11,359,175 B2 | 6/2022 | Ohsaka et al. | |
| 2011/0117634 A1 | 5/2011 | Halamish et al. | |
| 2018/0280976 A1* | 10/2018 | Lelièvre | B01F 25/4331 |
| 2018/0291330 A1* | 10/2018 | Shen | C12M 25/02 |

(Continued)

FOREIGN PATENT DOCUMENTS

| | | |
|---|---|---|
| CN | 103003450 B | 6/2014 |
| CN | 108795753 A | 11/2018 |

(Continued)

*Primary Examiner* — Brian R Gordon
(74) *Attorney, Agent, or Firm* — Best & Flanagan LLP (57) ABSTRACT

Present invention is related to a tumor microenvironment on chip or a biochip for cell therapy having a carrier, a first cell or tissue culture area and a second cell or tissue area imbedded within the carrier. The present invention provides a biochip successfully cooperating micro fluidic technology and cell culture achieving the goal for detecting or testing the function of cell therapy for cancer or tumor.

6 Claims, 13 Drawing Sheets

(56) References Cited

U.S. PATENT DOCUMENTS

| | | | |
|---|---|---|---|
| 2019/0054461 A1* | 2/2019 | Varadarajan | B01L 3/5085 |
| 2019/0064168 A1* | 2/2019 | Handique | B01L 7/52 |
| 2020/0268683 A1* | 8/2020 | Li | A61K 51/0497 |
| 2020/0385666 A1 | 12/2020 | Mogi | |
| 2022/0243172 A1* | 8/2022 | Chung | C12N 5/06 |
| 2022/0395828 A1* | 12/2022 | Zhao | B01L 7/52 |

FOREIGN PATENT DOCUMENTS

| | | |
|---|---|---|
| CN | 111630147 A | 9/2020 |
| CN | 112739809 A | 4/2021 |
| TW | I593798 B | 8/2017 |
| TW | I670369 B | 9/2019 |
| TW | I724028 B | 4/2021 |

\* cited by examiner

TUMOR MICROENVIRONMENT ON CHIP

FIELD OF INVENTION

The present invention is related to a tumor microenvironment on chip or also called biochip, more particularly to a biochip for cell therapy purpose and a production method of making the same.

The biochip provided by the present invention will mainly be described hereinafter for cell therapy, especially for treating cancer with cell therapy as a primary embodiment below. However, the biochip provided by the present invention does not limit to such single application or this certain of use. Other applications with similar or equivalent mechanisms or function should also be covered within the claimed scope of the present invention.

BACKGROUND OF THE INVENTION

Biochips have risen rapidly in recent years with plenty scientists and developers devoted to such field. The concept of the biochips is mainly focused on a microfluidic technology embedded with semiconductor processing methods as the core but applied to medical purpose as an in vitro analysis of human body or exploring human physiological activities and disease for seeking effective treatment options.

Although development of biology in the past ten decades has greatly improved and also promoted human life with more healthier approaches, large amount of biological experiments still remain at a simple transitional cell culture level. However, this over-simplified research method is not only difficult to truly reflect the complex functions of tissues and organs in the human body, but also difficult to reflect the true conditions of human tissues and organs to external stimuli.

Although animal experiments can provide more comprehensive studies and analysis of cells, tissues and organs, there are still significant deficiencies such as species differences between experimental animals and humans. As advanced countries such as the United States or the European Union are gradually banning animal experiments due to humility issue, how to provide an actual testing method has pushed the development of biochips. It has provided an innovative solution based on the level of tissues and organs to solve the old cell cultures and animal experiments.

By the micro-system on the biochip mimicing the real tissues or organs, scientists can simulate a real connection between the different tissues and organs of the human body in vitro and predict the human body's response to drugs or different external stimuli. This has broaden applications and prospects in fields of life sciences, medical research, new drug development, drug prediction, beauty cosmetics testing, and biological defense.

On the other hand, biochips currently do not have any application applied to cell therapy for cancer treatment. This technology mainly dedicates to repair damaged tissues by utilizing specific healthy cells from the owner body. It is well-known that stem cell therapy and immune cell therapy have been used in the treatment of stroke, cancer, spinal injury, burns and beauty, etc. It is eager to introduce biochip technology into cell therapy that will overcome or substantially ameliorate at least one or more of the deficiencies of a prior art, or to at least provide an alternative solution to the problems. It is to be understood that, if any prior art information is referred to herein, such reference does not constitute an admission that the information forms part of the common general knowledge in the art.

SUMMARY OF THE INVENTION

In order to solve the inaccuracy of traditional cell culture and the animal experiment is gradually banned from many countries, the present invention provides a biochip for cell therapy to solve or at least provide a substituted solution.

In accordance, a first concept of the present invention is a biochip for cell therapy comprises a carrier; a first cell or tissue culture area is provided on the carrier; and a second cell or tissue culture area is further a recess from a bottom of the first cell or tissue culture area.

In accordance, the present invention provides a production method of the biochip comprises steps of: producing a biochip as claimed in claims 1 to 3 by three-dimensional printing, reversal molding, laser processing, computer numerical control processing or injection molding; and placing the second cell in the second cell or tissue culture area and covering with the intermediary cell.

In accordance, the present invention has the following advantages:
1. The biochip for cell therapy provided by the present invention has been tested with proving ability of successfully culturing target cancer cells, endothelial cells and T cells thereon. T cells have been observed of passing through the endothelial cells and migrated into cancer cells causing cytotoxic and inhibit the growth of cancer cells.
2. The biochip for cell therapy provided by the present invention can be used as an in vitro test module to improve the inaccuracies or limitations of the conventional cell culture and animal experiments, and is successfully applied to cancer cell therapy and drug screening.

DETAILED DESCRIPTION OF THE PREFERRED EMBODIMENTS

Reference will now be made in detail to the present preferred embodiments of the invention, examples of which are illustrated in the accompanying drawings. Wherever possible, the same reference numbers are used in the drawings and the description to refer to the same or like parts. It is not intended to limit the method by the exemplary embodiments described herein. In the following detailed description, for purposes of explanation, numerous specific details are set forth in order to attain a thorough understanding of the disclosed embodiments. It will be apparent, however, that one or more embodiments may be practiced without these specific details.

As used in the description herein and throughout the claims that follow, the meaning of "system", "device", "unit" and/or "module" are just an expression to distinguish different components, parts or assemblies in the present invention. It is not intended to limit the present invention to certain type of expressions.

As used in the description herein and throughout the claims that follow, the meaning of "a", "an", and "the" may include reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to.

A flow chart might be implanted by the present invention for illustrating details of the production method. However, steps being arranged in the flow chart are not necessary to be limited in these certain orders. It might be acceptable without effecting the claimed function of the present invention to comprise extra steps or remove some steps from the flow chart.

First Embodiment

Figure 1:
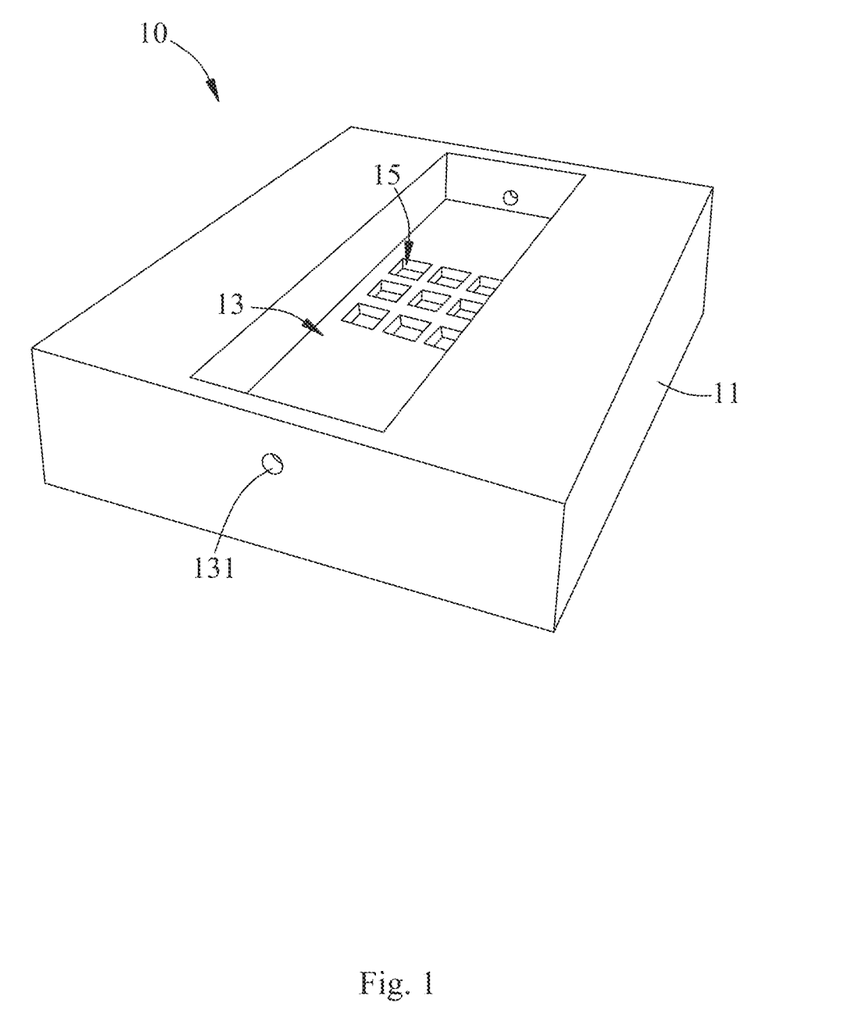
FIG. 1 is an illustration of a first preferred embodiment in accordance to the present invention.

With reference to FIG. 1, a first preferred embodiment of the biochip 10 for cell therapy of the present invention includes a first cell or tissue culture area 13 and a second cell or tissue culture area 15 provided on a carrier 11. The first cell or tissue culture area 13 and the second cell or tissue culture area 15 are preferred to be in a fluid communication with each other, and a through hole 131 communicating with outside is provided in the first cell or tissue culture area 13.

As shown in FIG. 1, the carrier 11 of the biochip 10 is defined from its top surface downwardly with two stages of concaved spaces. The first space began from the top surface of the carrier 11 is the first cell or tissue culture area 13. The first cell or tissue culture area 13 is provided with two through holes 131 on a side wall of the first cell or tissue culture area 13, preferably symmetrically. Then, from the bottom of the first cell or tissue culture area 13 partly or completely downwardly, the second stage of concaved space is defined as at least one second cell or tissue culture area 15. In this embodiment, as shown in FIG. 1, the carrier 11 is a longitude extended block material. The first cell or tissue culture area 13 is a recess concaved from the top surface inwardly from the carrier 11. From the bottom of the first cell or tissue culture area 13, number of 9 second cell or tissue culture areas 15 are concavely provided in a 3*3 array. However, the number of the first and second cell or tissue culture areas 13, 15 is not limited in the present invention. It might be 1, 2, or even multiple numbers being setup in the present invention.

Figure 2:
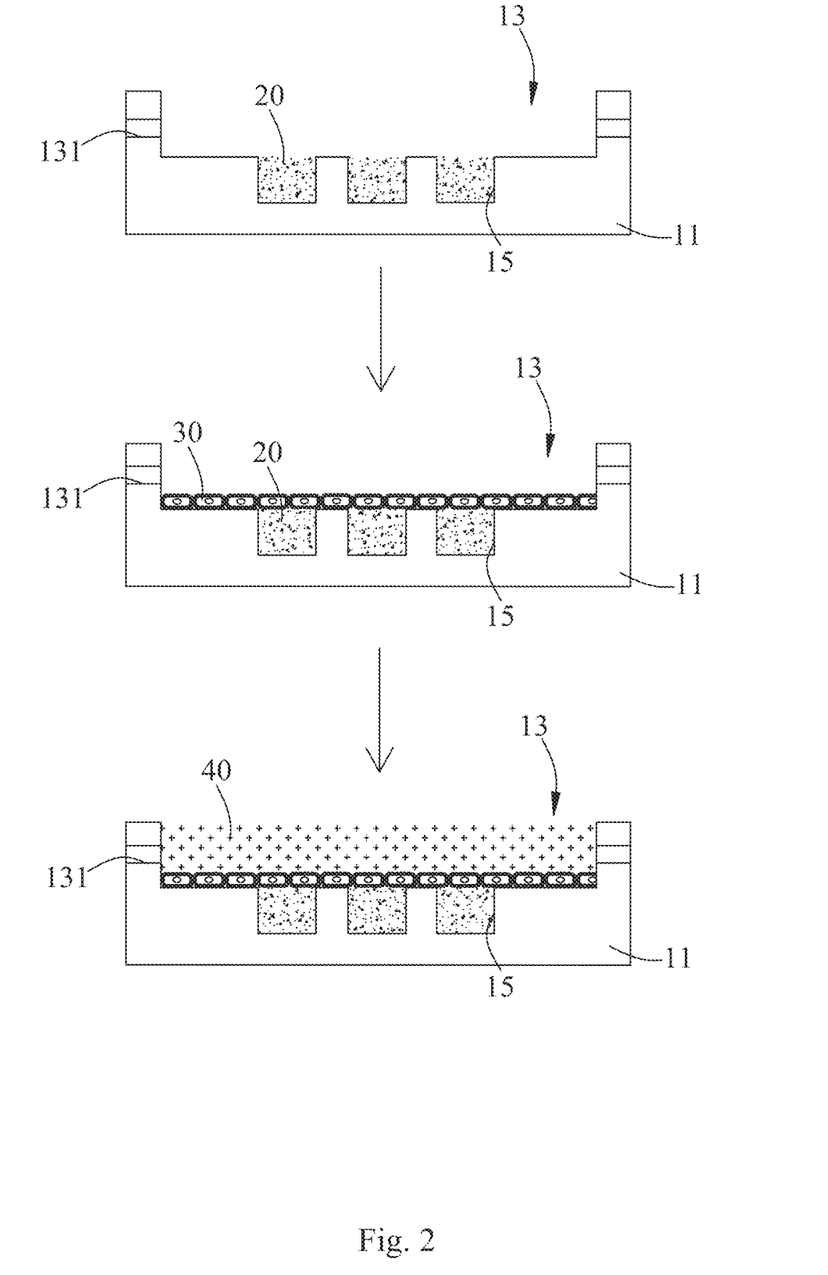
FIG. 2 is a flow chart illustration of configuration for uploading cells in the first preferred embodiment in accordance to the present invention.

With reference to FIGS. 1 and 2, to assemble the above-mentioned biochip 10 of the present invention with suitable cells or tissues, the preferred embodiment is stated as following. A second cell 20 are firstly provided to be placed into the second cell or tissue culture area 15 mixed with preferably a culture medium including a culture fluid, culture gel or in a form of cell blocks, etc. If the carrier 11 contains multiple second cell or tissue culture area 15, different kinds of second cells 20 could be placed in different second cell or tissue culture area 15 as desired. An intermediary cell 30 is further cultured by covering the surface of the second cell or tissue culture area 15 where the second cell 20 is located as also to be on a bottom of the first cell or tissue culture area 15. A first cell 40, preferably with suitable culture medium, like gel or cell blocks is cultured in the first cell or tissue culture area 13 with fluid perfusion or just static placement to become as the biochip 10 for cell therapy as described in the present invention. The symmetrical through hole 131 in the first cell or tissue culture area 15 serves as an inlet and an outlet respectively for giving and taking nutrition, medicine, metabolite or other therapeutically effective components in and out from the biochip 10 for the first cell 40.

It is worth noting that the culture status of the first cell 40 in the first cell or tissue culture area 13 of the present invention may be dynamically presented with fluid perfusion or statically presented with simple cell culture. Although cell's responses of these two cultivations are different in the following validation tests, both of them still can achieve the claimed effects of the present invention.

A preferred embodiment of the second cell 20 comprises cancer cells (or tumor cells). The intermediary cell 30 comprises endothelial cells. The first cell 40 is preferred to have functions or abilities for applying to cell therapy, for example, autoimmune cells like NK cells, T cells, etc. The biochip 10 provided by the present invention can evaluate the effects of autoimmune cells for suppressing the cancer cells. The biochip 10 for cell therapy of the present invention is preferably produced by a 3D printing process for customized production with more flexibility and high precision, and all the aforementioned cells can be placed in their respective positions by a bioprinter automatically without human contact.

In the first embodiment, a mechanism or execution of a biochip 10 for cell therapy is that the endothelial cells of the intermediary cell 30 are servsed as human blood vessels. The cancer cells of the second cells 20 and the autoimmune cells as the first cells 40 are located respectively on both sides of the intermediary cell 30 (as on the both side of the human vessels). After culturing for a period of time, the results could be observed as confirming if the first cell 40 passed through the intermediary cell 30 reaching the second cells 20 as to act like a testing module mimicking real human body reaction. In some preferred embodiment, medicine or any suitable therapeutic components which could help to eliminate cancer cells can be further added to the culture medium of the first cells to evaluate the validation or function of the said medicine or any suitable therapeutic components.

Second Embodiment

Figure 3:
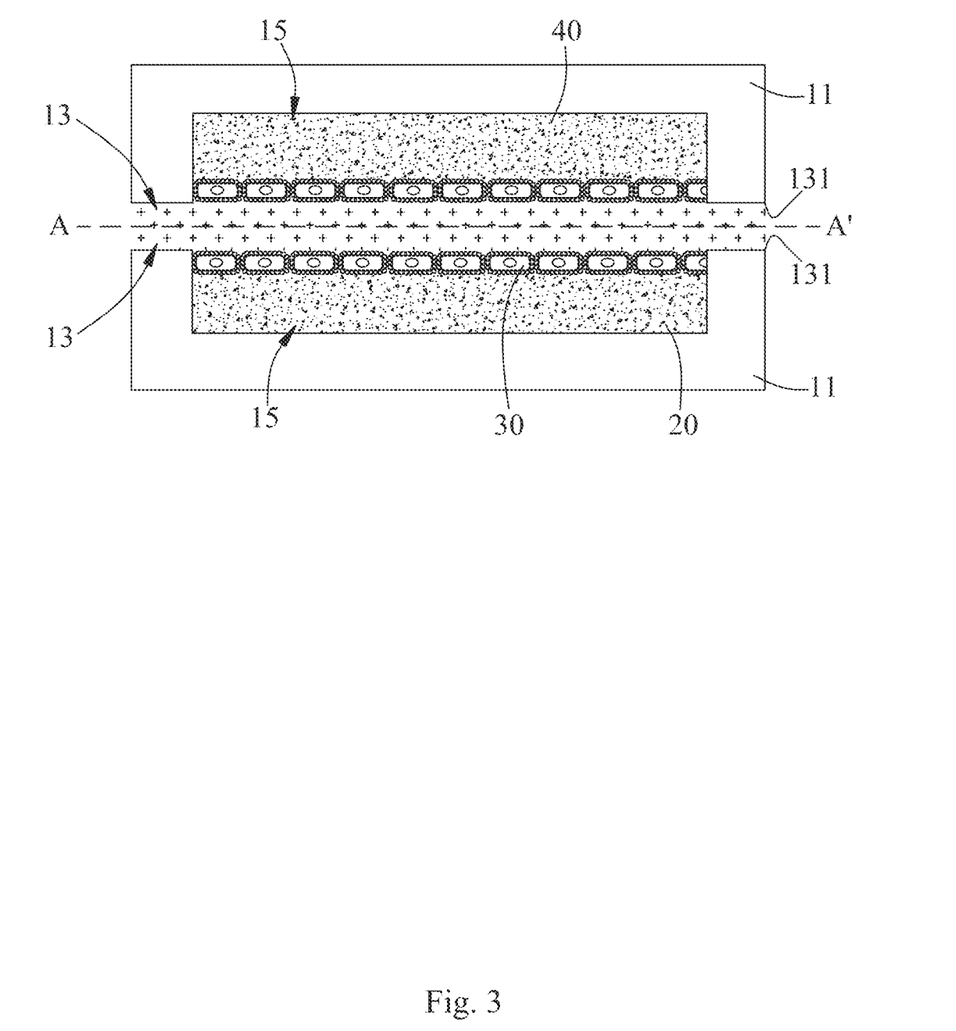
FIG. 3 is an illustration of a second preferred embodiment in accordance to the present invention.

A second embodiment of the biochip 10 for cell therapy of the present invention is based on the aforementioned first embodiment. However, a major difference between the first embodiment and the second embodiment is that the second embodiment has additionally symmetrical structure along with a dashed line AA' as shown in the cross-sectional view in FIG. 3. In this embodiment, the through hole 131 is connected in a symmetrical structure so that the first cell or tissue culture area 13 forms a channel being sandwiched by the second cell or tissue culture area 15 on both sides. The through holes 131 are still provided at both ends for communicating with outside environment. In this embodiment, cells configurations are preferred to be as following. The second cell 20 are placed in the second cell or tissue culture areas 15 on both sides. The intermediary cell 30 are cultured to cover the surface of the second cell or tissue culture areas 15 also from both sides. The culture medium or any therapeutic efficacy components are perfused from the two through holes 131. In this embodiment, the biochip 10 is design with more alike structure of human vessels tube for better testing results.

<Production Method>

The production method for aforementioned two embodiments of biochip 10 comprises steps of:

Step 1: the carrier 11 is processed by three-dimensional printing (3D printing), reversal molding, laser processing, computer numerical control (CNC) processing or injection molding;

Step 2: the second cell 20 is placed on the second cell or tissue culture area 15 and the intermediary cell 30 are covered to the surface of the second cell or tissue culture area 15.

Step 3: Optionally, the first cell 40 is perfused or placed in the first cell or tissue culture area 13.

The second cell 20, the intermediary cell 30 and the first cell 40 could be placed or cultured manually or utilizing an automated robotic arm to be filled at the right position similar to 3D printing or bio-printing.

The three-dimensional printing method (3D printing) described in the aforementioned step 1 may preferably be a fused deposition modeling (FDM) or light-curing three-dimensional printing method with suitable 3D image. Laser processing and CNC processing are performed by cutting pre-set recesses on the carrier 11 as a block material. The injection molding method is to inject a suitable resin material into a corresponding mold by an injection machine and cured with the final product.

Validation tests will be conducted for the two embodiments of the biochip 10 as described above.

<Validation Tests>

Figure 4A:
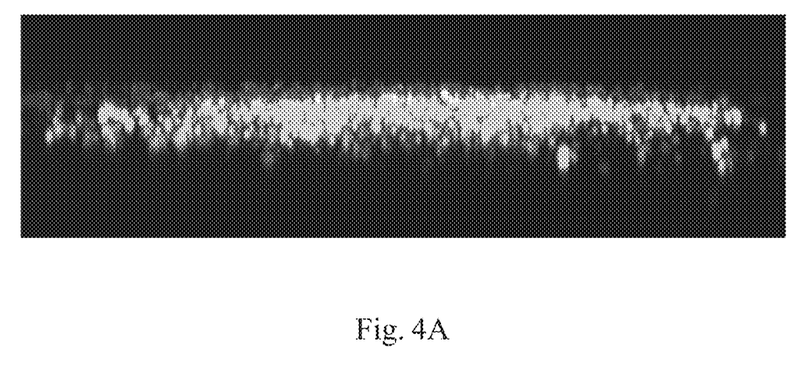
FIGS. 4A and 4B are immunohistochemistry of cells of the first preferred embodiment at the initial stage before culture in accordance to the present invention.
Figure 4B:
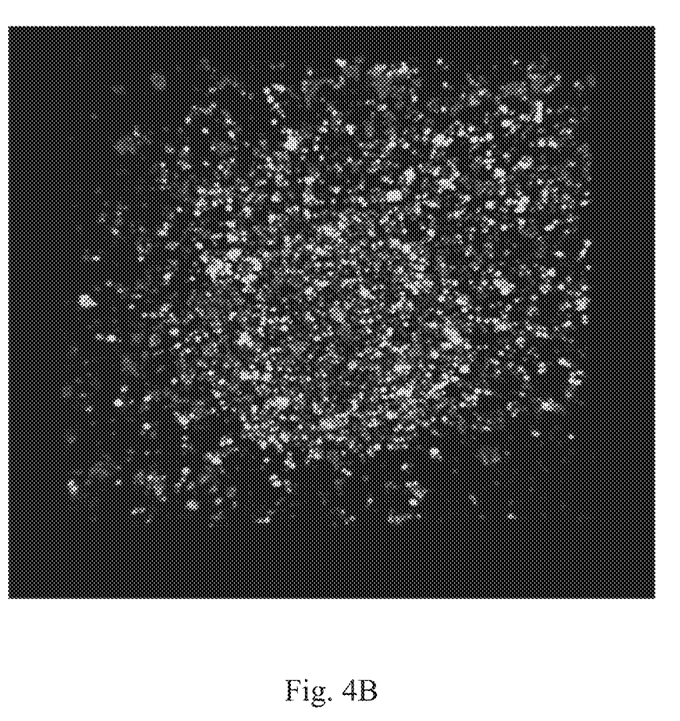
Figure 5:
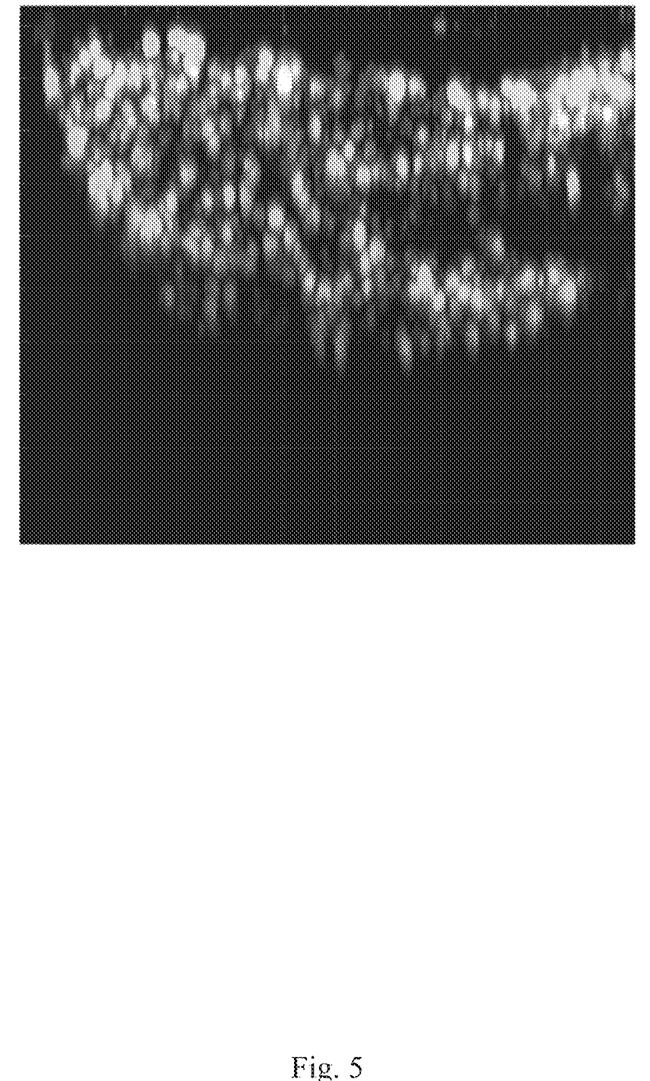
FIGS. 5, 6A, and 6B are immunohistochemistry of cells of the first preferred embodiment after culture in accordance to the present invention.
Figure 6A:
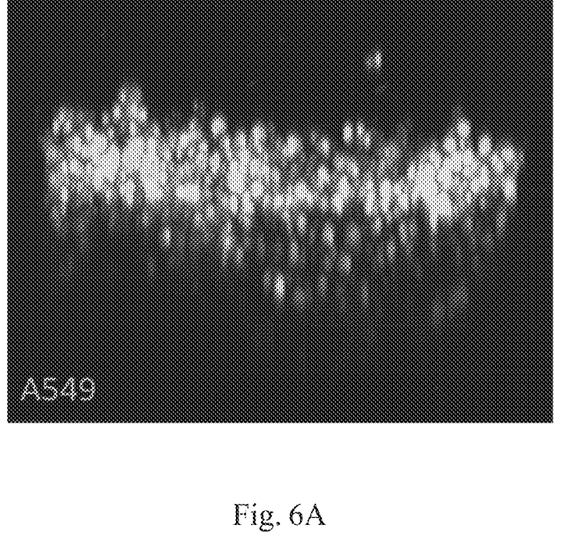
Figure 6B:
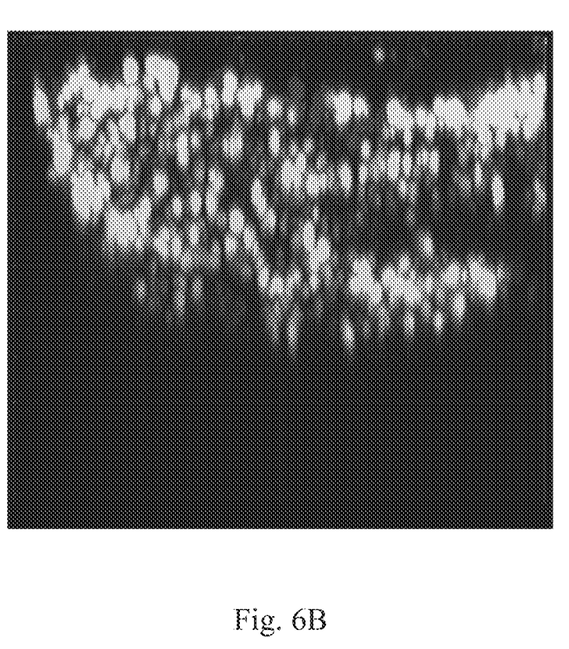

With reference to FIGS. 4A, 4B, and 5, serval immunohistochemistry images are provided by using the first embodiment of the present invention. In these immunohistochemistry images of the first embodiment, the second cell 20 is lung cancer cells (A549), and the intermediary cell 30 is endothelial cells (HUVEC) and the first cell 40 is T cells. As shown in FIGS. 4A and 4B, as the biochip 10 just assemble with the first, the second and the intermediary cells, immunohistochemistry images with fluorescent staining at an interface between the first cell or tissue culture area 13 and the second cell or tissue culture area 15 are presented. In FIG. 5, after culturing for period of time, immunohistochemistry images with fluorescent staining at the same site of the first cell or tissue culture area 13 and the second cell or tissue culture area 15 is presented. In FIGS. 4A and 4B, brighter color dots distributed at the bottom are the lung cancer cells and the litter darker color dots distributed at the top are endothelial cells. In FIG. 5, the T cells at the top can be observed successfully passing through the endothelial cells and distributed in the brighter cancer cells. It is confirmed that the biochip 10 provided by the present invention does have the function of simulating the circulation of human tissue cells and the T cell could successfully passing through the endothelial cells. As the culture time progress, as shown in FIGS. 6A and 6B, the immunohistochemistry images with fluorescent staining at the site of the second cell or tissue culture area 15 shows great amount of brighter T cells distributed among the darker cancer cells.

Figure 7:
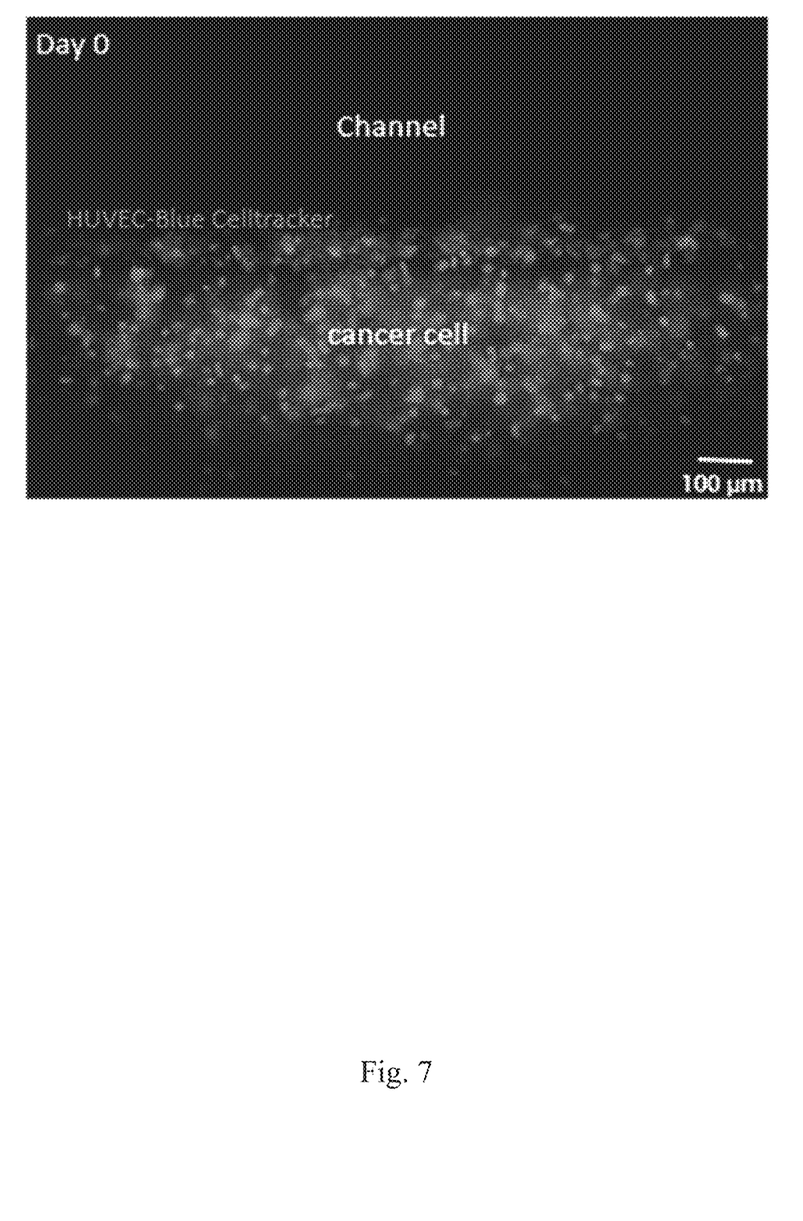
FIG. 7 is an immunohistochemistry of cells of the second preferred embodiment before culture in accordance to the present invention.

With reference to FIG. 7, an immunohistochemistry image is provided by using the second embodiment of the present invention. The second cell 20 is breast cancer cells (MDA-MB-231), the intermediary cell 30 is also endothelium Cells (HUVEC) and the first cell 40 is a T cell (GDT). As the biochip 10 just assemble with the first cell 40, the second cell 20 and the intermediary cells 30, immunohistochemistry image with fluorescent staining at an interface between the first cell or tissue culture area 13 and the second cell or tissue culture area 15 are presented in FIG. 7, brighter color dots distributed at the bottom are the breast cancer cells and the litter darker color dots distributed at the top are endothelial cells.

Figure 8A:
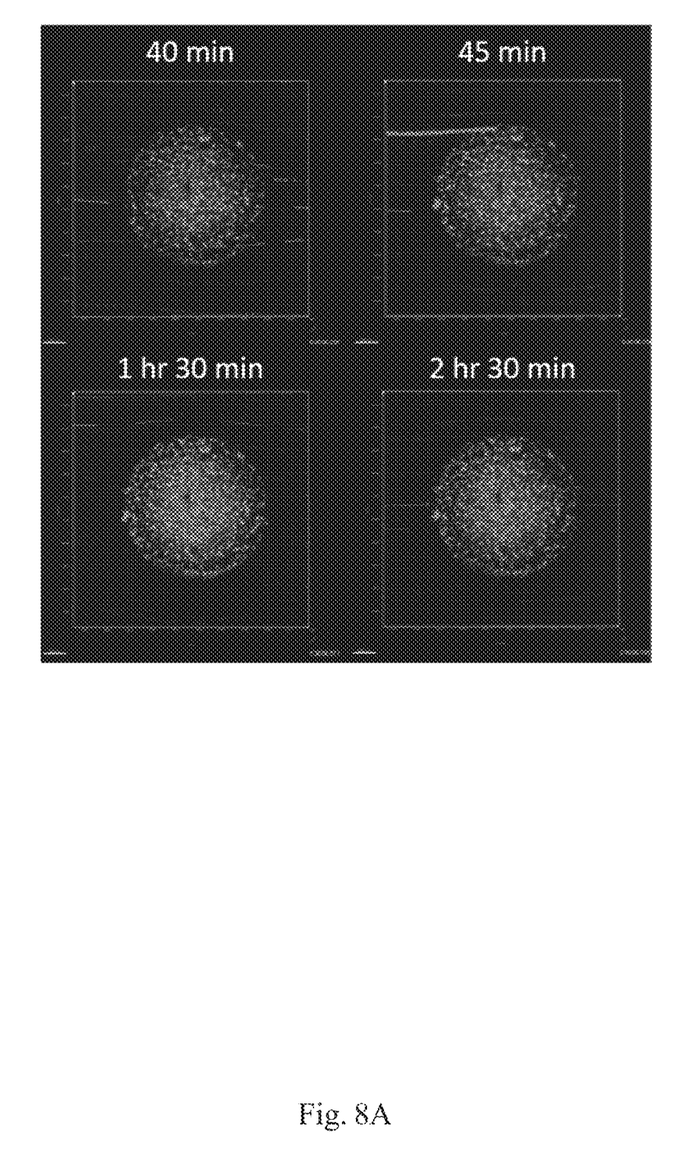
FIG. 8A is an immunohistochemistry of cells of the second preferred embodiment after culture in accordance to the present invention.

In this embodiment, the cells are cultured with dynamic perfusion with suitable fluid in the first cell or tissue culture area 13. As shown in FIG. 8A, after culturing for 40 minutes, 45 minutes, 1.5 hours, and 2.5 hours in the first day, the immunohistochemistry image can be observed with lighter color dots (which is T cells) at the lateral part. As the culture time going, more and more lighter color dots are attached to the second cell 20 a breast cancer cell with is presented as a spheroidal darker shape in the image.

Figure 8B:
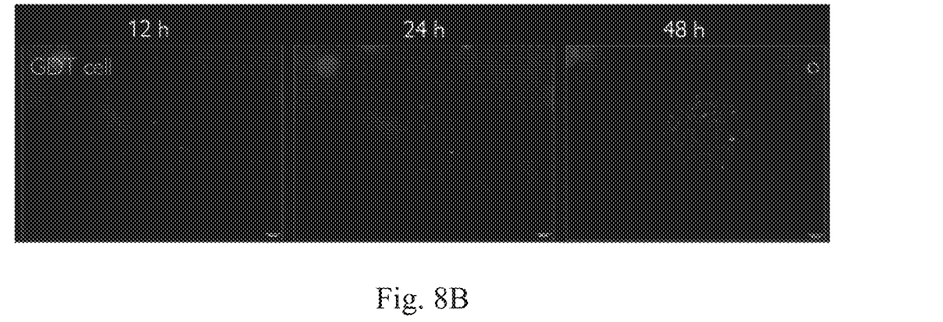
FIGS. 8B, 8C, and 8D are immunohistochemistry of T cells, cancer cells and the overlapping image of T cell and cancer cells after 12 to 48 hours culture in accordance to the present invention.
Figure 8C:
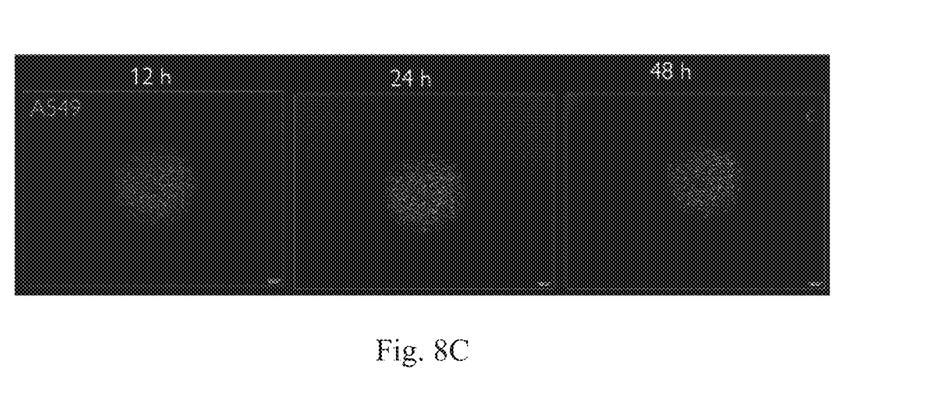
Figure 8D:
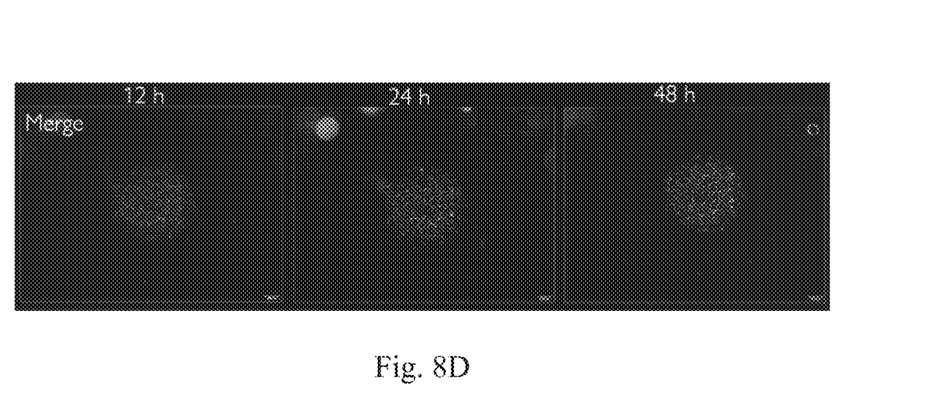

As shown in FIGS. 8B to 8D, by continuously perfusing fluid to T cells and cancer cells in the biochip 10 or a long time, the results show the states of the two cells after 12, 24, and 48 hours of perfusion, respectively. FIG. 8B is the immunohistochemistry image observed solely for T cells. The result shows that the brighter spots gradually increase and become obvious, indicating that T cells are indeed attached to the cancer cells. FIG. 8C is the immunohistochemistry image observed solely for cancer cell. The density of the spherical blob of the cancer cells gradually decreases and becomes hollow. FIG. 8D is a overlapped image of FIGS. 8B and 8C. It shows that the area of T cells in lighter dots distributed in the spherical cancer cells increases, and at the same time, the dead cancer cell with the brightest spots are shown. These test results show that T cells have successfully kill the cancer cells on the biochips 10 of the present invention. By utilizing the cancer cells from the target patient, the biochips 10 could be used as a test module or a platform for confirming if the patient's cancer cells have any response for the cell therapy before applying the treatment to the patient.

Figure 9:
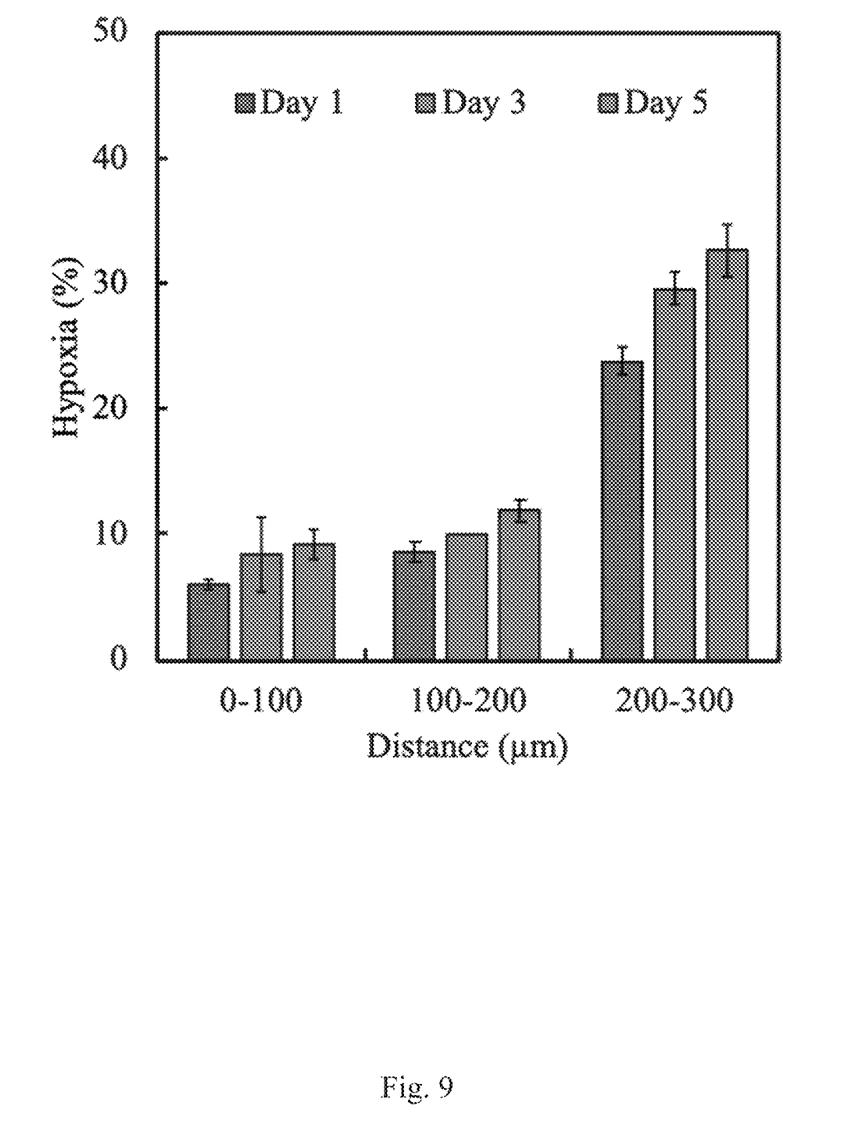
FIG. 9 is a diagram showing the culture condition differences in hypoxic cells caused by culture time and distance in accordance to the present invention.
Figure 10A:
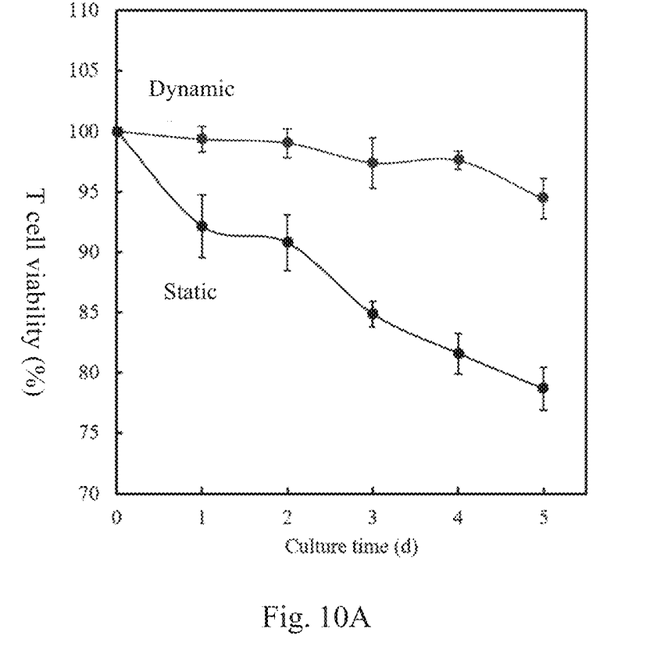
FIG. 10A is a diagram showing a condition of T cells being cultured under dynamic perfusion or static cultivation in accordance to the present invention.
Figure 10B:
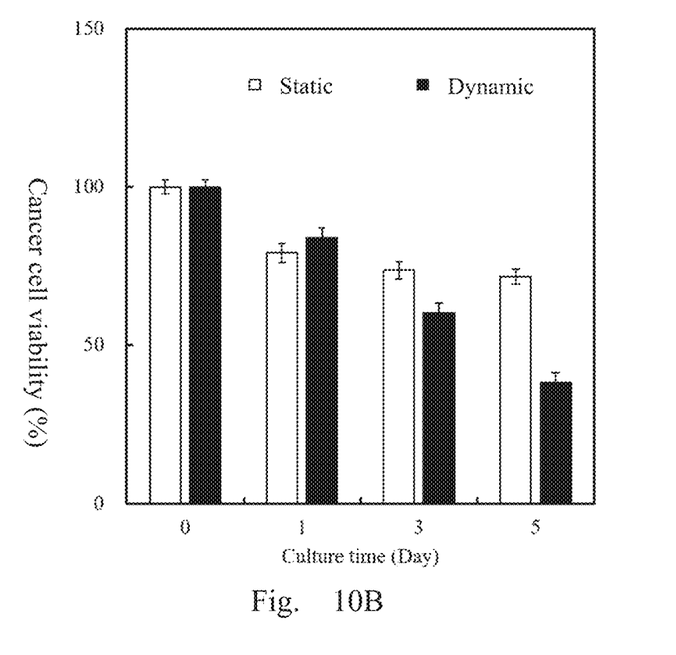
FIG. 10B is a diagram showing a condition of cancer cells being cultured under dynamic perfusion or static cultivation in accordance to the present invention.

As shown in FIG. 9, the result shows that distance factor from the endothelial cells also impact the cytotoxic ability to the T cell or hypoxia rate of cancer cells. FIG. 10A shows the culture result under dynamic perfusion of T cells. As the culture time increases, the survival rate of T cells is higher under dynamic perfusion culture condition. The survival rate of static culture for T cells otherwise decreases slightly but still remains applicable for the present invention. FIG. 10B also shows the cell viability rate of the cancer cells in the dynamic perfusion and static culture condition. The result shows that with the continuous supply of fresh and viable fluid (with fresh T cells), a more long-lasting (ie. 3, 5 days) and obvious of result for killing cancer cells by the T cells are presented. The static culture otherwise only shows a better cytotoxic ability at the beginning because of higher concentration or density being remained at same site of the culture medium. However, T cells are observed with gradually decreased cell viability and effectiveness due to the gradual sedimentation and stacking pressure under long-term culture, which also leads to a decline cytotoxic ability. However, both static culture or dynamic perfusion are all contained in the present invention with proven ability.

Figure 11:
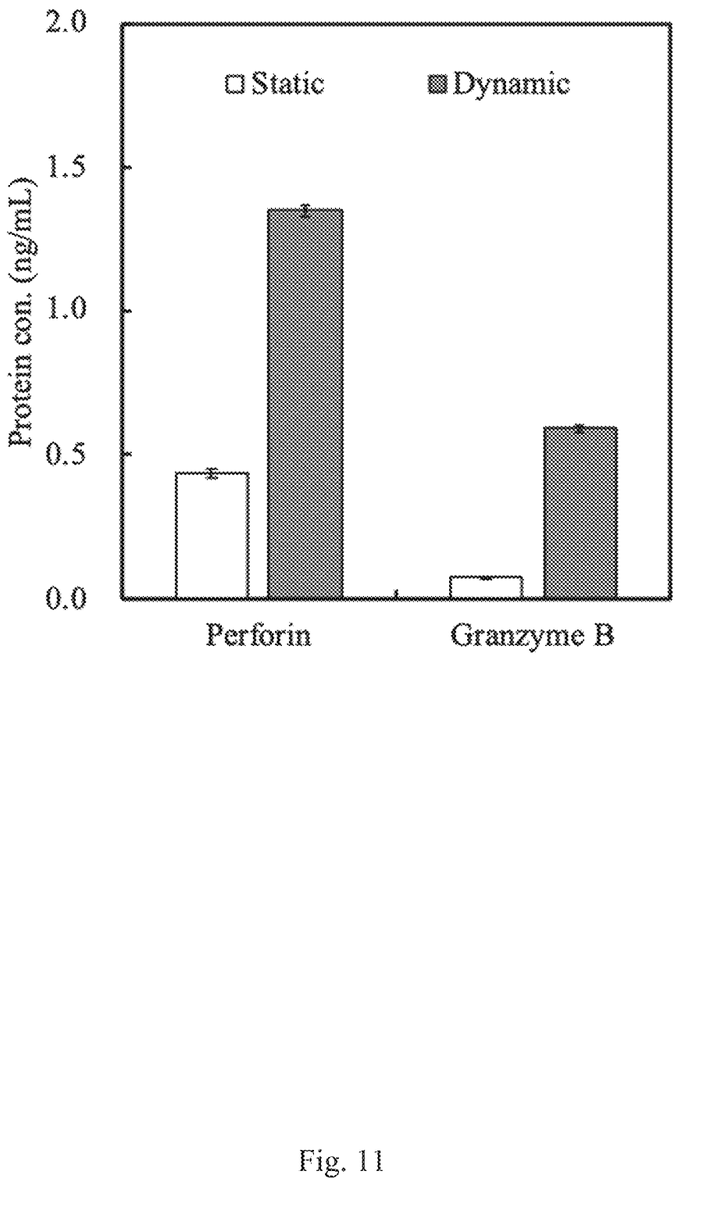
FIG. 11 is a diagram showing the content of dynamic toxicants produced by T cells being cultured under dynamic perfusion or static cultivation in accordance to the present invention.
Figure 12A:
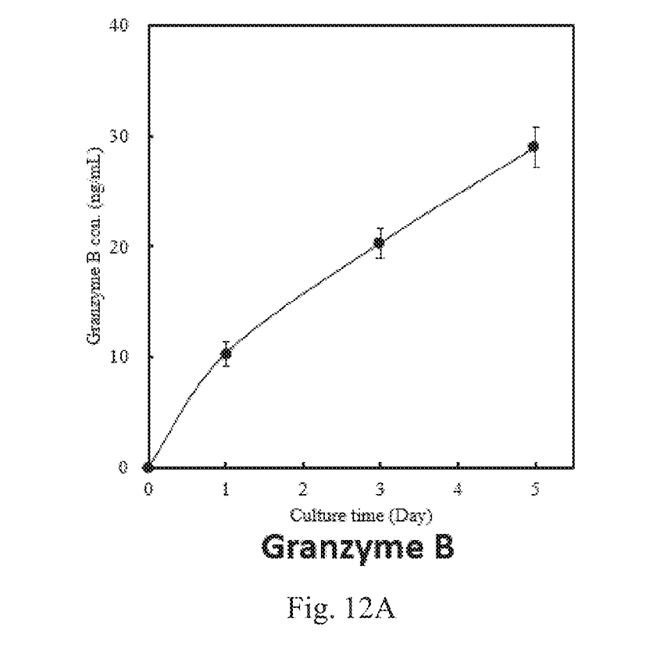
FIGS. 12A and 12B are diagrams of the content of dynamic toxicants produced by T cells being cultured under dynamic perfusion or static cultivation in a longer period of time in accordance to the present invention.
Figure 12B:
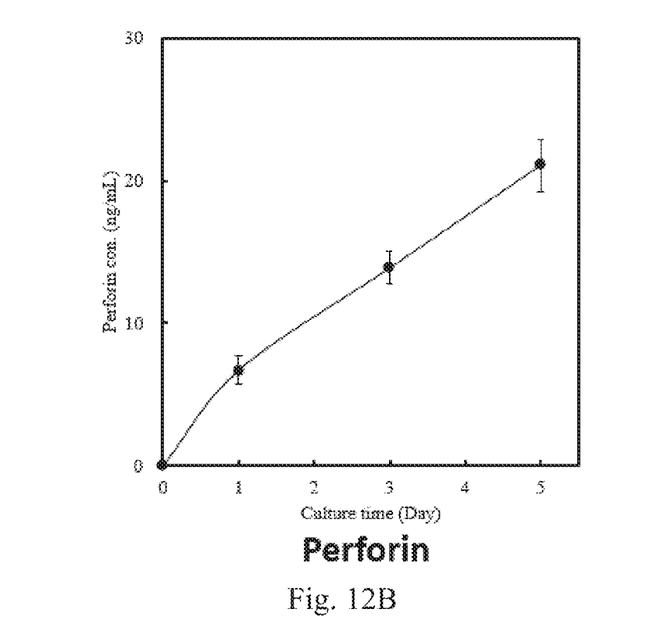

FIG. 11 shows the content of Perforin, Granzyme B produced by T cells under dynamic perfusion and static cultures. Two culture conditions are all proven with valid cytotoxic ability of T cells. Dynamic perfusion culture still shows a better result than static culture. FIGS. 12A and 12B especially show the increase in perforin content under dynamic perfusion for culturing with longer time.

The above specification, examples, and data provide a complete description of the present disclosure and use of exemplary embodiments. Although various embodiments of the present disclosure have been described above with a certain degree of particularity, or with reference to one or more individual embodiments, those with ordinary skill in the art could make numerous alterations or modifications to the disclosed embodiments without departing from the spirit or scope of this disclosure.

In order to simplify the disclosure of the present invention and facilitate the understanding of the embodiments, the present invention might combine multiple features into one embodiments or corresponded figures. However, this does not imply that the present invention requires full features described in the embodiment. In fact, it is possible that the claimed features might be less than the features being contained in the embodiment disclosed above.

In some embodiments, numbers or quantity might be used or limited to describe the present invention. It should be understood that such numbers or quantity used in the description such as "about", "approximately" or "substantially" is allowed to have differentials by ±20%. Correspondingly, in some embodiments, the numerical parameters might be referred to approximate values. Also, in some embodiments, the numerical parameter might be recorded to an effective digits.

The present invention may cited some reference including patent, patent application, publication and other materials like articles, books, specifications, publications, documents, etc. It should be understood that the definition and/or use of terms of the present invention shall be prevail if there is any inconsistency or conflict between the cited reference and the present invention.

Finally, it should be understood that the embodiments described in the present invention are only used to illustrate the operation or action of the preferred embodiments. Any suitable modifications or revisions may also fall within the scope of the present invention. Therefore, the present invention are not limited to the certain embodiments provided by this specification.

What is claimed is:

1. A biochip for cell therapy, the biochip comprising:
    a carrier having a top surface, a bottom surface, and a side wall;
    a first culture area being a first cavity recessed in the top surface of the carrier, the first culture area having a side wall and a bottom surface;
    a through hole extending through the side wall of the carrier and the side wall of the first culture area, the through hole positioned above the bottom surface of the first culture area, the through hole in fluid communication with the first culture area;
    at least one second culture area, each of the at least one second culture area being a second cavity recessed in the bottom surface of the first culture area;
    a second biological cell disposed in each of the at least one second culture area;
    a first middle layer comprised of a third biological cell, the first middle layer covering the bottom surface of the first culture area and extending over the at least one second culture area;
    a first biological cell disposed in the first culture area over the first middle layer; and
    the first middle layer is located between the through hole and the at least one second culture area.

2. The biochip as claimed in claim 1, further comprising a second middle layer, each of the first middle layer and the second middle layer having a first side and a second side, wherein the through hole extends through the first culture area in a first direction, the first middle layer and the second middle layer are respectively spaced apart along the first direction by the first culture area, the first side of the first middle layer disposed along the first culture area, the second side of the second middle layer disposed along the first culture area, and the second side of the first middle layer disposed along a first one of the at least one second culture area and the first side of the second middle layer disposed along a second one of the least one second culture area.

3. The biochip as claimed in claim 1, wherein: the second biological cell comprises cancer cells, the third biological cell comprises endothelial cells, and the first biological cell comprises autoimmune cells.

4. The biochip as claimed in claim 1, wherein: the second biological cell is comprised in the at least one second culture area with a second culture medium in a form of liquid, gel or cell block; and the first biological cell is comprised in the first culture area with a first culture medium in a form of liquid, gel or cell block.

5. A production method of a biochip comprising steps of:
    producing a first cavity recessed in a top surface of a carrier by three-dimensional printing, reversal molding, laser processing, computer numerical control (CNC) processing or injection molding, the first cavity defining a first culture area, the first culture area having a bottom surface and a side wall;
    producing a plurality of second cavities recessed in the bottom surface of the first cavity, each of the plurality of second cavities is a second culture area;
    producing a through hole in a side wall of the carrier, the through hole extending through the side wall of the carrier and the side wall of the first culture area, the through hole positioned above the bottom surface of the first culture area;
    placing a second biological cell in at least one second culture area of the plurality of second culture areas;

covering the at least one second culture area and the bottom surface of the first culture area with a middle layer having a third biological cell; and placing a first biological cell in the first culture area.

6. The production method as claimed in claim 5, wherein: the second biological cell comprises cancer cells, the third biological cell comprises endothelial cells, and the first biological cell comprises autoimmune cells.

* * * * *